(12) United States Patent
Segina et al.

(10) Patent No.: US 8,790,321 B2
(45) Date of Patent: Jul. 29, 2014

(54) APPARATUS, SYSTEM, AND METHOD FOR HARVESTING IMPROVED BONE GRAFT MATERIAL WITH REAMER-IRRIGATOR-ASPIRATOR (RIA) DEVICE

(75) Inventors: Daniel Nick Segina, Satellite Beach, FL (US); James Arthur Proctor, Jr., Melbourne Beach, FL (US)

(73) Assignee: Genesis Medical Devices, LLC, Indialantic, FL (US)

( * ) Notice: Subject to any disclaimer, the term of this patent is extended or adjusted under 35 U.S.C. 154(b) by 355 days.

(21) Appl. No.: 13/091,123

(22) Filed: Apr. 21, 2011

(65) Prior Publication Data
US 2011/0262405 A1 Oct. 27, 2011

Related U.S. Application Data

(60) Provisional application No. 61/326,234, filed on Apr. 21, 2010.

(51) Int. Cl.
*A61K 35/32* (2006.01)
(52) U.S. Cl.
USPC ............... 604/319; 604/19; 604/27; 604/35; 210/634; 210/645; 424/93.7
(58) Field of Classification Search
None
See application file for complete search history.

(56) References Cited

U.S. PATENT DOCUMENTS

| | | | |
|---|---|---|---|
| 7,008,394 B2 * | 3/2006 | Geise et al. | 604/6.15 |
| 7,011,852 B2 * | 3/2006 | Sukavaneshvar et al. | 424/532 |
| 2006/0273049 A1 * | 12/2006 | Leach et al. | 210/787 |
| 2007/0055282 A1 * | 3/2007 | Muschler | 606/92 |

OTHER PUBLICATIONS

Synthes Ltd., "Reamer/Irrigator/Aspirator (RIA). For intramedulary reaming and bone harvesting", http://www.synthes.com/MediaBin/US%20DATA/Product%20Support%20Materials/Brochures/SUSA/SUBRORIAJ8968B.pdf 2008, pp. 1-8.*

* cited by examiner

*Primary Examiner* — Laura Schuberg
(74) *Attorney, Agent, or Firm* — G. Philip J. Zies; Mark R. Malek; Zies Widerman & Malek (57) ABSTRACT

The present invention provides for the harvesting of specific materials in multiple stages of filtration of bone graft materials from a Reamer-Irrigator-Aspirator (RIA) Device, specifics of interconnected stages, related filtration materials, and techniques. The harvesting process collects large material in a first stage, and other materials of a limited geometric size in at least a second stage of filtration. Such material captured in the second stage may contain plasma, cellular elements including stem cells as well as growth factors and other particulate matter of a specific geometrically limited size, using various filtration approaches including centrifugation in some embodiments. Further embodiments of the invention provide for an improved tubing interface and management approach to ease use in the operating room. Filtration materials may include collagen based filters and may allow direct implant of small scale and larger scale matter in specific portions within the collagen itself.

26 Claims, 7 Drawing Sheets

APPARATUS, SYSTEM, AND METHOD FOR HARVESTING IMPROVED BONE GRAFT MATERIAL WITH REAMER-IRRIGATOR-ASPIRATOR (RIA) DEVICE

CROSS-REFERENCE TO RELATED APPLICATIONS

This application claims the benefit of provisional patent application Ser. No. 61/326,234, filed 21 Apr. 2010 by the present inventors.

FEDERALLY SPONSORED RESEARCH

Not Applicable

BACKGROUND

The present invention is in the technical field of medical devices. More particularly, the present invention is in the technical field of harvesting bone graft materials using a Reamer-Irrigator-Aspirator (RIA) Device. Currently, materials in the output stream from a RIA device, such as that provided by Synthes, are not fully and efficiently collected. While there have been some attempts to collect large scale material, other materials such as plasma, and other cellular elements are not currently collected and are discarded. Further, the approach used even to collect the large scale materials, essentially bone fragments, is not efficient for medical personnel to use in the operating room.

SUMMARY OF THE INVENTION

It is an object of this invention to provide for an improvement in the collection of bone graft or other materials from the output of a reamer-irrigator-aspirator device. It is a further object of this invention to provide for an improved tubing interface and management approach to ease use in the operating room. It is a further object of this invention to provide for an improved "stage 1" or large scale matter filtering system to retrieve bone fragments and other large scale matter from the output of the RIA device. It is a further object of this invention to provide for a second stage filtration or separation approach to separate the remaining small scale matter, including but not limited to cellular elements, from the irrigation water following the stage 1 filtration system. The current invention operates with a RIA device to provide a filtration approach to retrieve matter which is useful during bone graft harvesting and other procedures. The RIA device reams a bone such as a femur. The RIA device is connected to an improved hosing system where a bi-lumen hose allows for easier management of the hosing in the operating room. One tube of the bi-lumen hosing provides water to the RIA to perform irrigation. The other hose receives the output of the RIA, which consists of water, large scale matter, and small scale matter including cellular elements in some embodiments. The large scale matter has a significant amount of bone fragments. The small scale matter contains a significant amount of plasma, stem cells, marrow material, and further additional elements which may include growth factors, depending on the porosity of the filter mechanism. The tube receiving the waste is connected to the stage 1 filter which filters out the stage 1 material. The filter in this case is a re-usable mesh or porous filter plate. The plate may be removed, and the collected stage 1 material used for bone grafts, or other uses. The output of the stage 1 filter is passed via another tube in one embodiment to a stage 2 filter or separator. Such a separator may be another filtering mechanism, or a centrifuge type device. When a centrifuge is used, a filter is used to remove the stage 2 material. This filter may be made of collagen, such that after collection of the stage 2 materials, the cylindrical collagen filter may be removed from the centrifuge, cut open, and laid flat on a stage 2 material pad. This pad may be combined with the stage 1 material, and used directly in the body for the grafting process, as collagen will dissolve at a later time. The alternative stage 2 filtration approach is to use a filter box, with a collagen filter. In another embodiment, a plurality of filters may be used, each targeted at retaining particulate matter of a desired geometry. In such cases any combination of porosities of each pair of filter stages may be utilized such that a specific range of particulate size is retained in the stage 2 filter or subsequent combination of any two cascaded filters.

Note that the specific examples provided are not intended to be limiting but are specific embodiments of the invention. Various alternative materials and processes may be used as known in the art.

DETAILED DESCRIPTION OF THE DRAWINGS

Figure 1A:
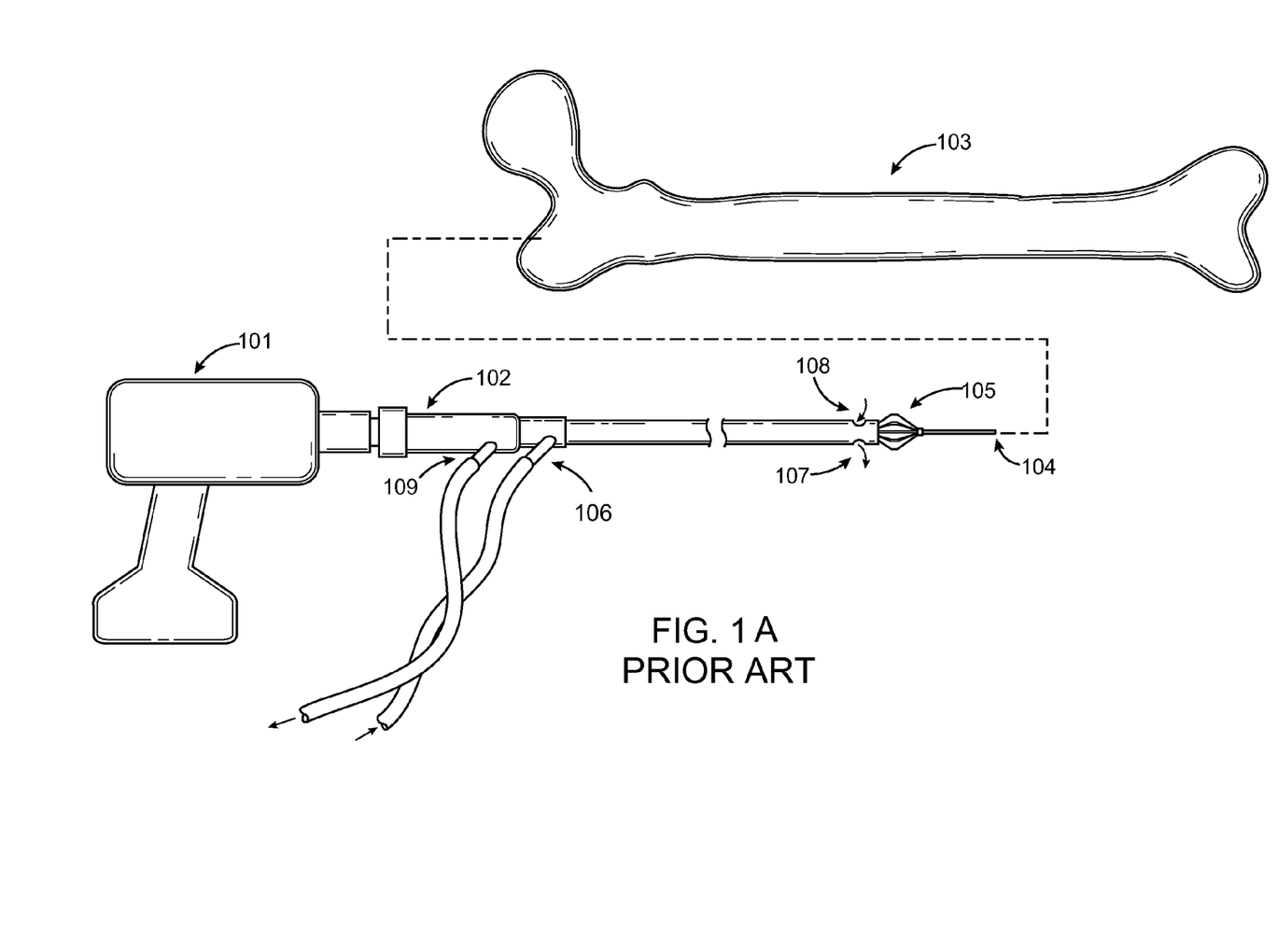
FIG. 1A is a diagram of the prior art RIA device.
Figure 1B:
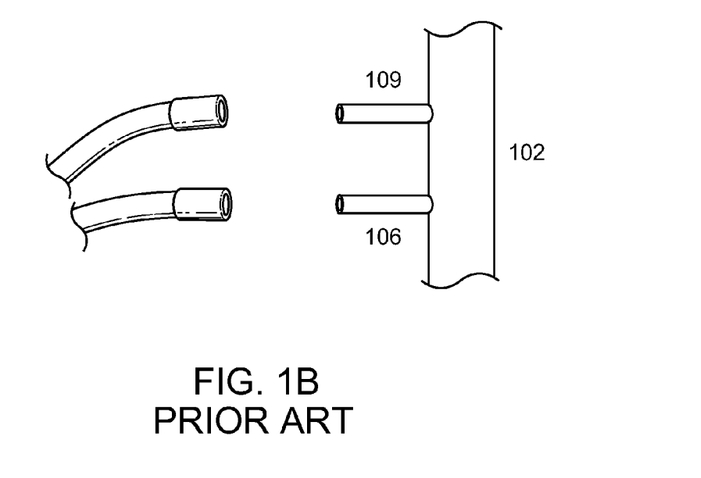
FIG. 1B is a diagram of the prior art RIA device tubing interface.

Referring to FIG. 1A, the depiction of the RIA which stands for Reamer Irrigator Aspirator. Depicted is a power source 101, a drill of any variety used within the operating room. The RIA device 102 is designed as a medullary bone graft harvesting device. The bone graft material would be harvested from the medullary canal of a native human femur 103 using the RIA device 102. A guide wire 104 is inserted into the medullary canal providing a guide for the RIA device 102 to remain within the medullary canal. The reamer head 105 is designed to cut the bone that is currently being harvested by the device. Through Port 106, the entry portal, saline is pumped into the device exiting out of Port 107. Suction is applied to the device through port 109, providing an avenue for fluid as well as bone graft material to exit the medullary canal via Port 108. It is then tunneled through Port 109 to a collection device or to the waste suction canister within the operating room. FIG. 1B is a depiction of the current device in larger scale at the region where the suction as well as irrigation ports meet with the RIA device 102. The RIA device with Port 106, labeled 102, is the port allowing for saline to float within the device and Port 109 being the port providing suction and an avenue for the evacuation of material from the medullary canal.

Figure 2:
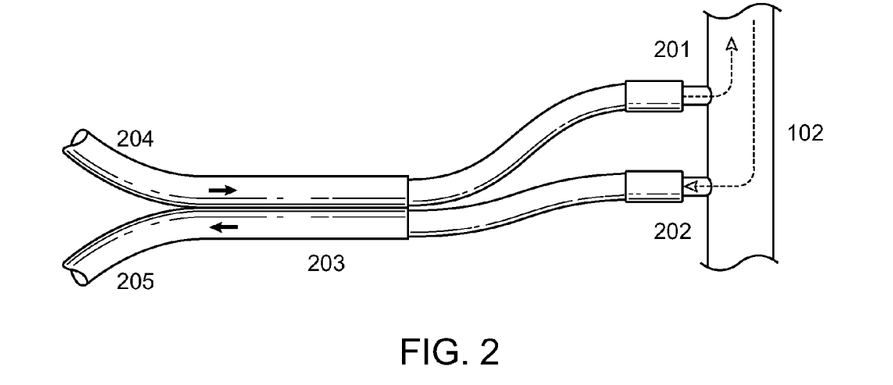
FIG. 2 shows the bi-lumen tube conned to a tube port in a RIA or other device

FIG. 2 is a depiction of the improved tubing system in one embodiment of this current invention. Depicted is the RIA device 102 with modified coupling Zones 201 as well as 202. 201 would be the coupling point for saline inflow into the RIA device 102; whereas, Port 202 would provide for efflux and evacuation of fluid as well as bone graft material that is applied via suction. The suction source would be obtained through a source available within the operating room. The tubing is coupled 203 to provide for less entanglement and more streamlined use within the operating room. These tubes would branch allowing for filtration/separation canisters, to be described later. Tube 204 would provide an inflow source for saline whereas Tube 205 would provide suction as well as an egress pathway for bone graft as well as saline or other fluids.

Figure 3:
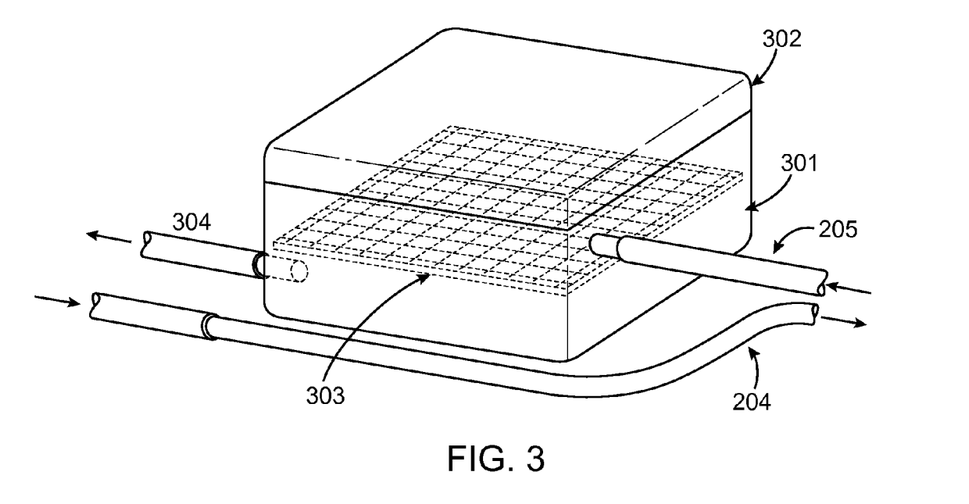
FIG. 3 shows the improved stage 1 filter with the water irrigation hose bypassing the filter (not integrated).

FIG. 3 depicts an embodiment of a modified Stage 1 filter for the collection of materials from the harvesting site. Saline and bone graft material would flow into the device via Tube 205. The device container, 301, would contain a hinged lid 302. Within the container 301, would be a Removable Porous Filter Device, 303, that is porous in nature to capture large bone graft material but provide for the flow through of saline, blood products, plasma, cells, and growth factors, and other particulate matter of a specific geometrically limited size. The material would be drawn through the filter via suction applied through Port 304. Also depicted in FIG. 3 would be Tubing 204 that would allow for saline to flow to the RIA device 102 and provide irrigation to facilitate the evacuation of bone graft material.

Figure 4:
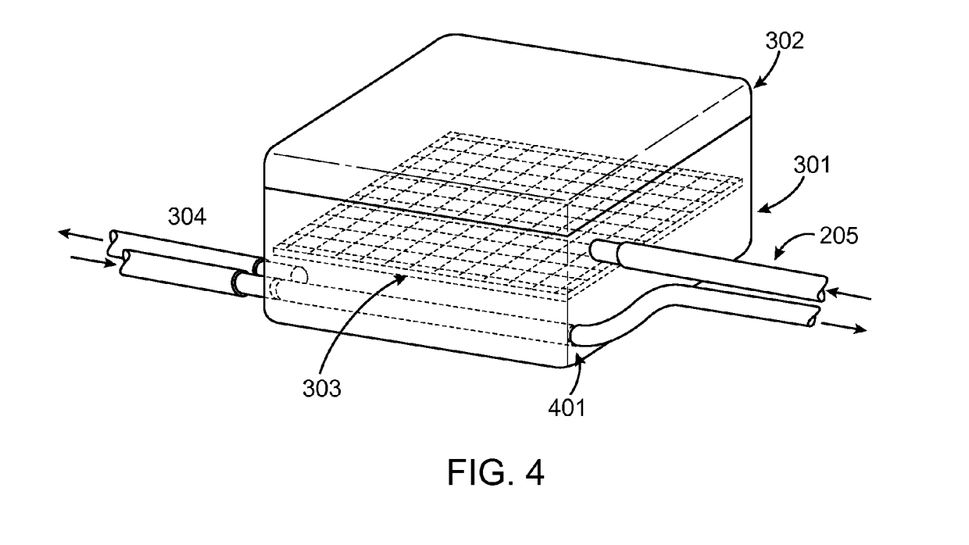
FIG. 4 shows the Stage 1 filter with an integrated pass through irrigation source hose for use with the bi-lumen tubing.

FIG. 4 is an alternative embodiment of the Stage 1 filter. Tube 401 would be contained within the Filter Device container, 301, once again avoiding significant entanglement and providing for more efficient use within the operating room. The remaining portion of the device would function very similar as the device in FIG. 3. A hinged lid, 302, providing access to Porous Filter 303, would catch material entering via Port 205 once again allowing for saline, blood products, plasma, cells, growth factors and other particulate matter of a specific geometrically limited size to pass through and be drawn out via Port 304.

Figure 5:
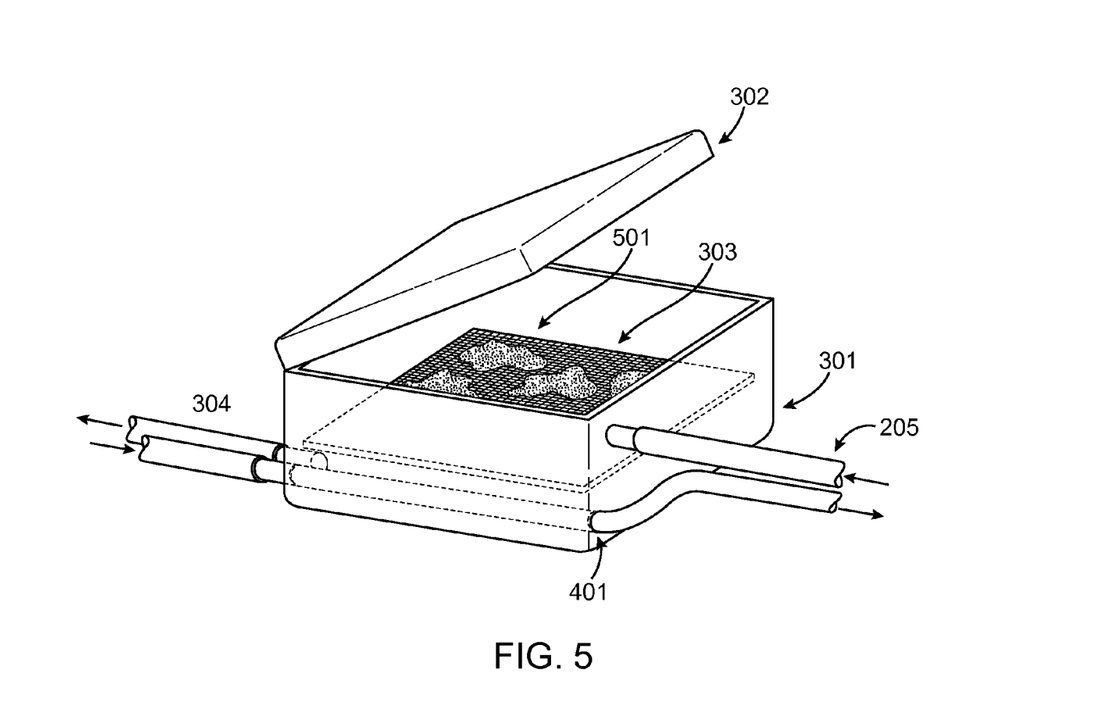
FIG. 5 shows the stage 1 filter with the lid open, and stage 1 material inside.

FIG. 5 shows one depiction of the initial stage filter with additional details noted. Through Tube 205 saline as well as graft material evacuated from the medullary canal would enter Stage 1 container 301. The lid now hinged open, depicted at 302, allows for access to Removal Filter 303 containing Bone Graft Material 501. The remaining portion of the fluid, containing blood products, plasma, cells, growth factors and other particulate matter of a specific geometrically limited size would be evacuated via suction, through Tube 304.

Figure 6:
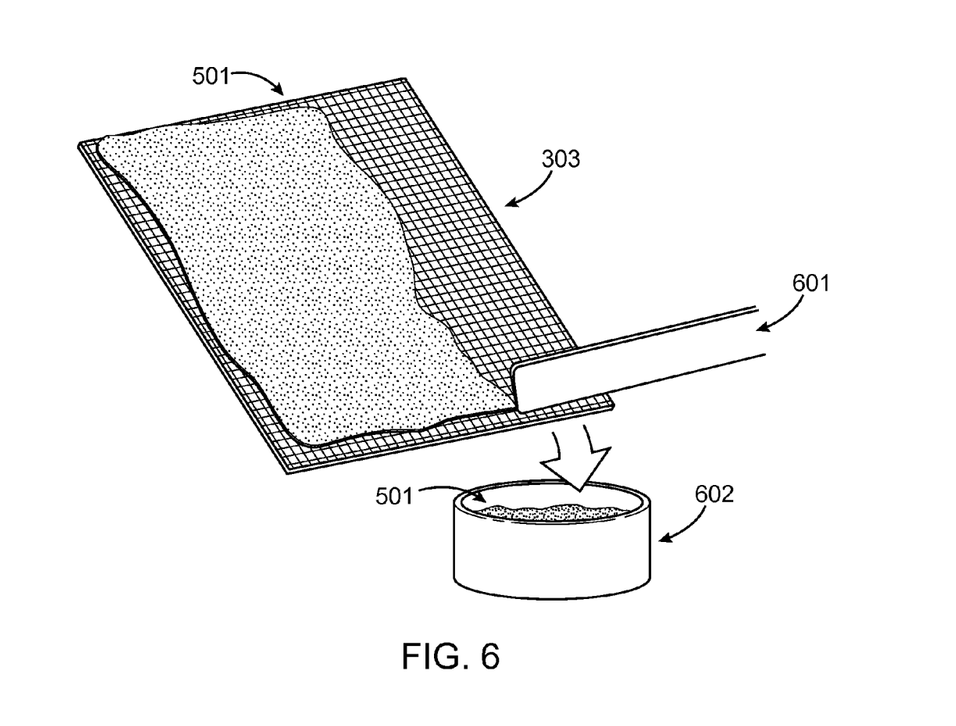
FIG. 6 shows the removed filter plate from the stage 1 filter with the stage 1 material being collected from the filter plate into a canister for later use.

FIG. 6 depicts the removal of the material off of Porous Filter 303. Bone Graft Material 501 would then be removed via Spatula Device 601 into Container 602. These Devices, 601 as well as 602, would be sterile and used within the operative field. The Collection Container 602 provides for a sterile container to contain the Bone Graft Material 501 for later re-implantation at the desired clinical site.

Figure 7:
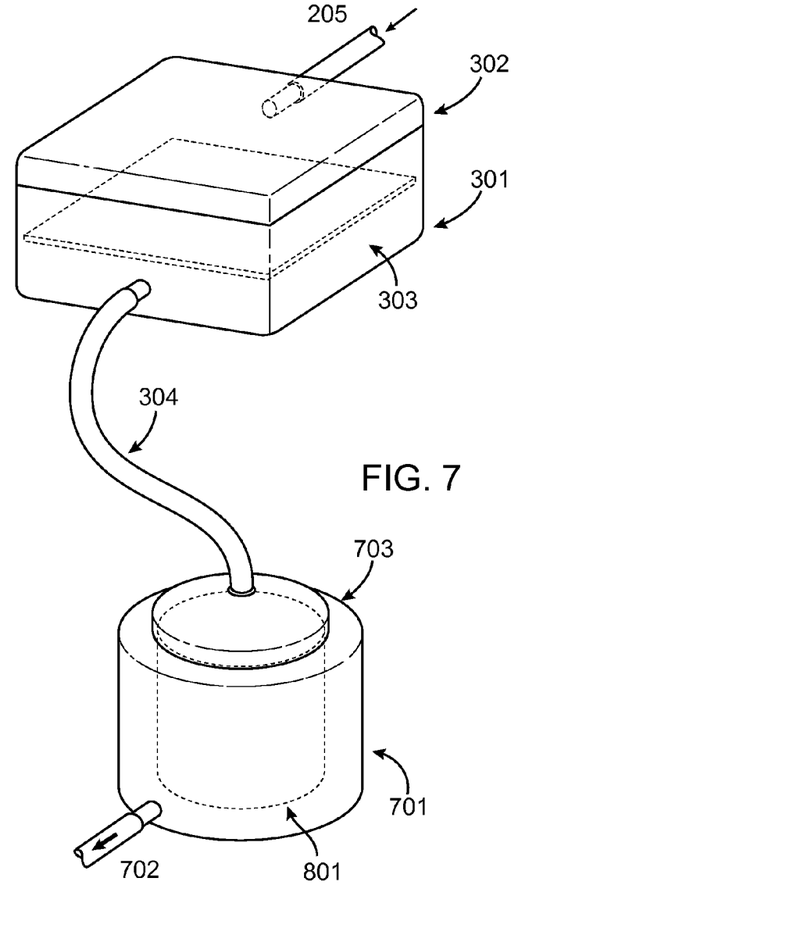
FIG. 7 shows the stage 1 filter connected to a stage 2 collector centrifuge, with a collagen sponge or filter cylinder inside in one embodiment of the invention.

FIG. 7 represents one embodiment of the second stage filtration system which would be designed to remove excess water yet retain additional graft material including but not limited to blood products, plasma, cellular bone marrow/stem cell elements, as well as growth factors and other particulate matter of a specific geometrically limited size. Depicted in FIG. 7 is the initial Stage Filter 303 contained within the Filtration container 301 covered by Lid 302. Initial material harvested from the RIA device 102 would enter the container via Tube 205. Large bone graft material would be trapped by Filter 303 allowing for the pass through/flow through of the remaining material through Tube 304. This material once again would represent blood products, plasma, and cellular elements including stem cells as well as growth factors and other particulate matter of a specific geometrically limited size. This material would then enter Centrifugal Filtration Device 701. This device would contain a porous filtration capturing membrane 801. It will be covered and contained within the centrifugal filtration device via Lid 703. The porous filtration capturing membrane 801 would be porous in its design to allow for capturing of blood products, plasma, cellular elements/stem cells, as well as growth factors and other particulate matter of a specific geometrically limited size, yet provide for the separation of fluid. This separation would then allow for a concentration of the graft elements and further to extract fluid from the system via centrifugation. The fluid may exit via Tubing 702 connected to an evacuation port in the various embodiments of the second stage filter as illustrated, for example, FIG.7.

Figure 8:
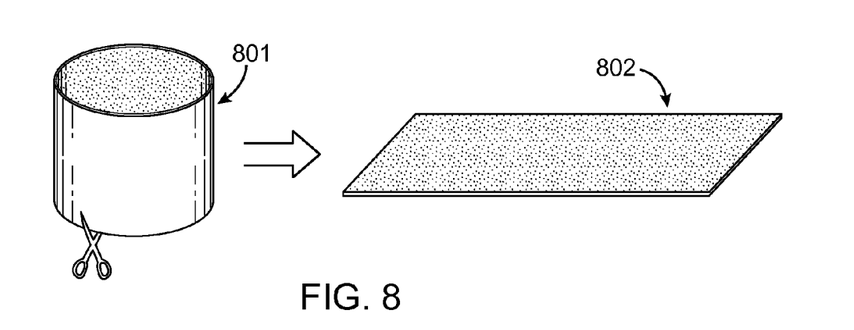
FIG. 8 shows the collagen filter removed from the centrifuge after collection, then cut into a flat "pad" of stage 2 material on the collagen filter or sponge in one embodiment.

FIG. 8 is a detailed depiction of the porous filtration capturing membrane within the Filtration Device 701. The cylindrical porous filtration capturing membrane 801 would be removed from Centrifugal Filtration Device 701 and cut to provide for a rectangular surface and function as a graft impregnated membrane for re-implantation within the patient.

Figure 9:
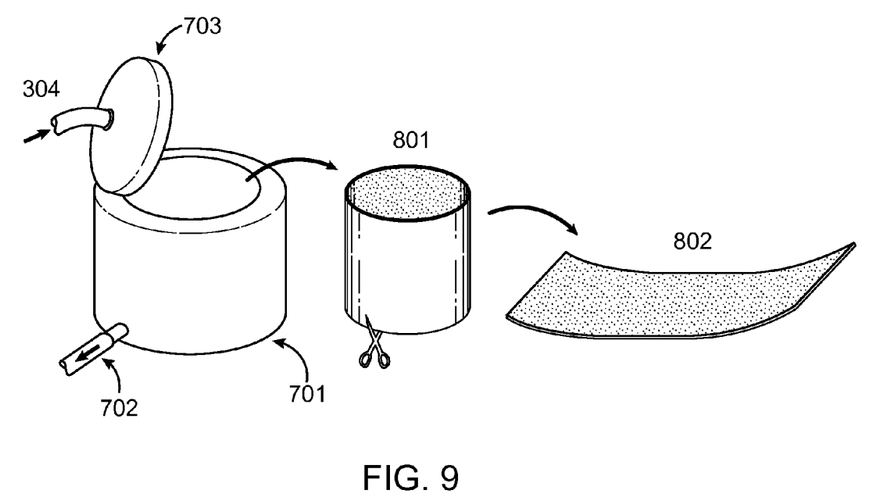
FIG. 9 shows the collagen or other filter material removed from the centrifuge, cut and laid flat as a stage 2 pad.

FIG. 9, once again, provides for a drawing of this process starting with the Centrifugal Filtration Device 701 that is sealed via Lid 703. Material filtered through the first stage filtration system enters via Tube 304. After a centrifugal filtration process takes place, within 701, the material is trapped within the porous filtration capturing membrane 801 which is porous in nature to provide for the capture of blood products, plasma, cellular elements including stem cells, as well as growth factors and other particulate matter of a specific geometrically limited size, but allow for the pass through of fluid that would exit via Tubing 702 connected to an evacuation port in the various embodiments of the second stage filter as illustrated, for example, in FIG.9. The porous filtration capturing membrane 801 could then be cut to size and later implanted within the patient.

Figure 10:
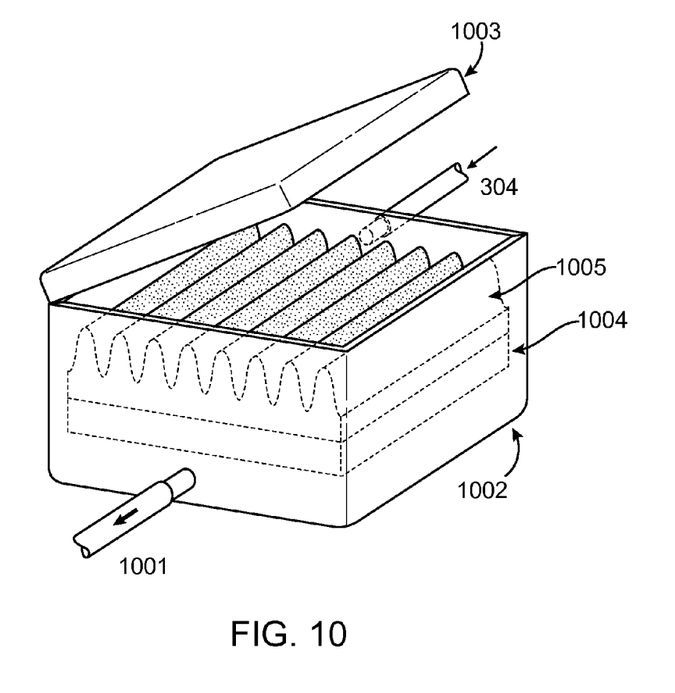
FIG. 10 shows an alternative stage 2 collector using a filtration system, containing a collagen or other materials filter plate or sponge.

FIG. 10 represents an alternative embodiment of the second stage filter. This filter would be designed for a more passive filtration process facilitated by vacuum negative pressure. Filtration Canister 1002 would contain a Hinged Lid 1003. Material exiting the first stage filter would enter the device via Tube 304. The undulating surface depicted as 1005 would be a filtration surface undulated for increasing surface area. It would reside on top of a porous yet Hydrophilic Membrane 1004 that would facilitate the extraction of fluid. The retention of blood products, plasma, cellular elements including stem cells, growth factors and other particulate matter of a specific geometrically limited size, would take place on the second stage (or any subsequent stage) filtration surface 1005. Excess fluid would then be evacuated via Tube 1001 connected to an evacuation port in the various embodiments of the second stage filter as illustrated, for example, in FIG. 10.

Figure 11:
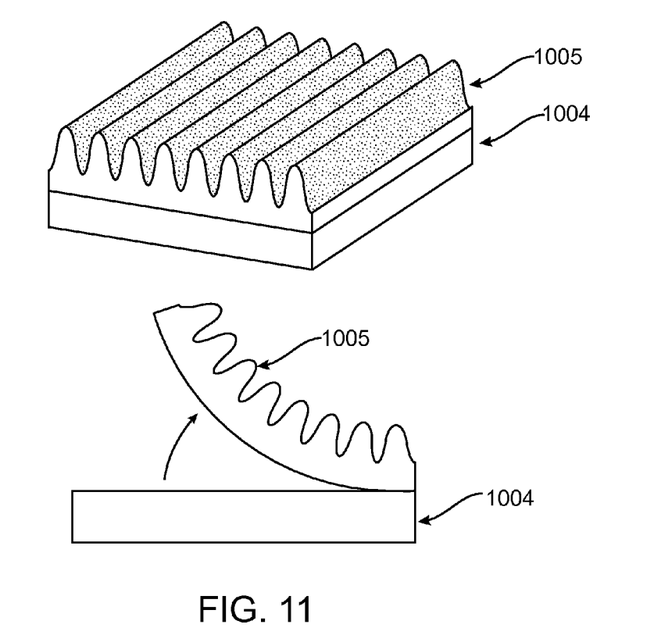
FIG. 11 shows the collagen filter being removed from the stage 2 filter, for use of the retained stage 2 materials.

In FIG. 11 a more detailed depiction of the second stage filter and hydrophilic membrane is depicted. The undulating Second Stage Filter 1005 would initially lie on top of porous Hydrophilic Membrane 1004. The Filtration Surface 1005 would then be peeled away from hydrophilic/porous Surface 1004 after it has been exposed to the second stage graft/fluid material. This surface would then be available for implantation within the desired clinical setting.

Figures 12, 13:
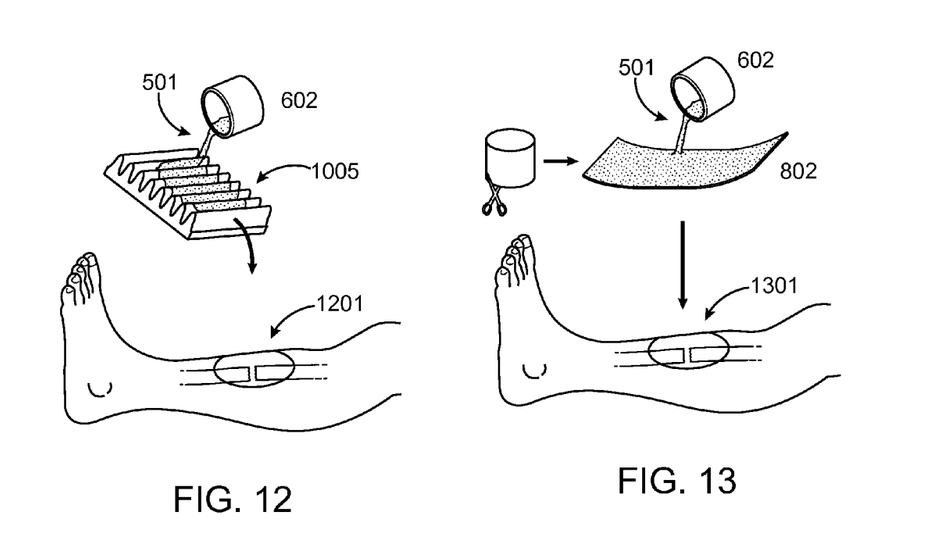
FIG. 12 shows stage 1 material in one embodiment being added to the stage 2 materials on a collagen filter, pad, or sponge and use as part of a bone graft in a patient. In this case the collagen filter, or sponge would be placed inside the patient along with the stage 1 and stage 2 materials, which may be modified in proportions. The filter, in one embodiment, would dissolve at a later time.
FIG. 13 shows an alternative embodiment of stage 1 materials being added to the stage 2 materials on a collagen filter, pad, or sponge and use as part of a bone graft in a patient.

FIG. 12 represents the final combination of material from the first as well as second stage of filtration, or any combination of a plurality of filtration stages. Material from the first stage of filtration, depicted as 501, and being contained within Sterile Container 602, would then be placed on top of Undulating Porous Sponge 1005. This would become a combination graft of large fragments of bone graft material from stage 1 combined with desired blood products, plasma, cellular elements/stem cells, growth factors and other particulate matter of a specific geometrically limited size. This combined graft can then be used in the desired clinical location. The location being depicted in FIG. 12 as 1201, a tibial bone graft site, although other site may be desired An alternative embodiment of the combined graft would be depicted in FIG. 13 that would provide for a combination of material from the first stage filtration as well as material captured via centrifugal filtration device and contained within the porous filtration capturing membrane 801. Material from the first stage of Filtration 501 would be removed from Container 602. It would then be placed on the cut porous filtration capturing membrane 801, which would contain blood products, plasma, cellular elements including stem cells as well as growth factors and other particulate matter of a specific geometrically limited size. This would then be made available for implantation within a desired clinical bone graft site depicted as a tibial site 1301 in FIG. 13, although other site may be desired.

What is claimed is:

1. A method for the collection of materials from a medullary bone graft source utilizing a reamer irrigator aspirator device, and a plurality of filters, the reamer irrigator aspirator device utilizing an irrigation fluid supply and a suction source, the method comprising:

connecting, by a first connecting tube, an input of a first stage filter container containing a first stage filter of the plurality of filters to an output of the reamer irrigator aspirator device;

passing a flow of materials suspended in an irrigation fluid harvested by the reamer irrigator aspirator device through the first connecting tube;

filtering, by the first stage filter, the flow of materials suspended in the irrigation fluid, wherein the first stage filter possesses a first particulate size selectivity to separate a first stage retained material from the flow of materials suspended in the irrigation fluid to provide a first stage output flow of materials suspended in the irrigation fluid;

passing the first stage output flow of materials suspended in the irrigation fluid through an output of the first stage filter container;

connecting, by a second connecting tube, an input of a second stage filter container containing a second stage filter of the plurality of filters to the output of the first stage filter container;

filtering, by the second stage filter, the first stage output flow of materials suspended in the irrigation fluid, wherein the second stage filter possess a second particulate size selectivity to separate a second stage retained material from the first stage output flow of materials suspended in the irrigation fluid to provide a second stage output flow of materials suspended in the irrigation fluid, wherein the second stage particulate size selectivity includes particulate sizes less than those included with the first particulate size selectivity; and accepting, by the second stage filter, the first stage retained material, to produce a combined graft product;

wherein the second stage filter container includes an evacuation port allowing for an open system to permit the flow of materials suspended in the irrigation fluid to be evacuated from the second stage filter container in a continuous process;

wherein the continuous process includes the first stage filter container receiving an additional flow of materials suspended in the irrigation fluid from the first connecting tube simultaneously with the second stage filter container providing the second stage output flow of materials suspended in the irrigation fluid to the evacuation port of the second stage filter container;

wherein the second stage filter is constructed utilizing a biodegradable-material-based filter.

2. The method of claim 1, wherein the first connecting tube is a bi-lumen connecting tube.

3. The method of claim 1, wherein the first particulate size selectivity allows for the collection of bone fragments, and allows for the passing of one or more of irrigation fluid, plasma, stem cells, growth factors, and cellular matter as the first stage output flow of materials suspended in the irrigation fluid.

4. The method of claim 3, wherein the second particulate size selectivity, allows for the collection of one or more of plasma, stem cells, growth factors, and cellular matter, and allows for the passing of the irrigation fluid, as the second stage output flow of materials suspended in the irrigation fluid.

5. The method of claim 4, wherein the step of filtering, by the second stage filter, utilizes a centrifuge to separate at least a portion of the irrigation fluid from the second stage retained material.

6. The method of claim 4, wherein the evacuation port is distinct from the second stage filter container input.

7. The method of claim 1, wherein the second stage filter is constructed utilizing a collagen-based filter.

8. The method of claim 1, wherein the step of filtering, by the second stage filter, utilizes a hydrophilic material aided by suction to separate the second stage retained material from the first stage output flow of material suspended in the irrigation fluid to provide the second stage output flow of material suspended in the irrigation fluid.

9. The method of claim 1, further comprising the step of implanting, by a medical professional, the combined graft product into a patient.

10. A method for the collection of materials from a medullary bone graft source utilizing a reamer irrigator aspirator device, the reamer irrigator aspirator device utilizing an irrigation fluid supply and a suction source, the method comprising:

connecting, by a first connecting tube, an input of a first stage filter container containing a first stage filter to an output of the reamer irrigator aspirator device;

passing a flow of materials suspended in an irrigation fluid harvested by the reamer irrigator aspirator device through the first connecting tube;

filtering, by the first stage filter, the flow of materials suspended in the irrigation fluid, wherein the first stage filter possesses a first particulate size selectivity to separate a first stage retained material from the flow of materials suspended in the irrigation fluid to provide a first stage output flow of materials suspended in the irrigation fluid;

passing the first stage output flow of materials suspended in the irrigation fluid through an output of the first stage filter container;

connecting, by a second connecting tube, an input of a second stage filter container containing a second stage filter to the output of the first stage filter container;

filtering, by the second stage filter, the first stage output flow of materials suspended in the irrigation fluid, wherein the second stage filter possess a second particulate size selectivity to separate a second stage retained material from the first stage output flow of materials suspended in the irrigation fluid to provide a second stage output flow of materials suspended in the irrigation fluid, wherein the second stage particulate size selectivity includes particulate sizes less than those included with the first particulate size selectivity; and accepting, by the second stage filter, the first stage retained material, to produce a combined graft product;

wherein the second stage filter container includes an evacuation port to permit the second stage output flow of materials suspended in the irrigation fluid to be evacuated from the second stage filter container in a continuous process;

wherein the continuous process includes the first stage filter container receiving an additional flow of materials suspended in the irrigation fluid from the first connecting tube simultaneously with the second stage filter container providing the second stage output flow of materials suspended in the irrigation fluid to the evacuation port of the second stage filter container.

11. The method of claim 10, wherein the first connecting tube is a bi-lumen connecting tube.

12. The method of claim 11 wherein the evacuation port is distinct from the second stage filter container input.

13. The method of claim 10, wherein the first particulate size selectivity allows for the collection of bone fragments, and allows for the passing of one or more of irrigation fluid, plasma, stem cells, growth factors, and cellular matter.

14. The method of claim 13, wherein the second particulate size selectivity allows for the collection of one or more of plasma, stem cells, growth factors, and cellular matter, and allows for the passing of the irrigation fluid.

15. The method of claim 14, wherein the second stage filter utilizes a centrifuge to separate at least a portion of the irrigation fluid from the second stage retained material.

16. The method of claim 14, wherein the second stage filter is constructed utilizing a biodegradable-material-based filter.

17. The method of claim 14, wherein the second stage filter is constructed utilizing a collagen-based filter.

18. The method of claim 14, wherein the second stage filter collects bone fragments from the first stage filter to produce a combined graft product.

19. The method of claim 14 wherein the second stage filter is constructed utilizing a material compatible with being implanted into a human.

20. The method of claim 10, wherein the second stage filter utilizes a hydrophilic material aided by suction to separate the second stage retained material from the first stage output flow of material suspended in the irrigation fluid to provide the second stage output flow of material suspended in the irrigation fluid.

21. The method of claim 10, wherein the combined graft product is useable for implantation into a patient.

22. The method of claim 21 wherein the second stage filter is constructed utilizing a material compatible with being implanted into a human.

23. The method of claim 22 further comprising the step of implanting the combined graft product into a patient.

24. The method of claim 1 wherein the second stage filter is constructed utilizing a material compatible with being implanted into a human.

25. The method of claim 24 further comprising the step of accepting, by the second stage filter, the collected bone fragments from the first stage filter, to produce a combined graft product.

26. The method of claim 25 further comprising the step of implanting the combined graft product into a patient.

* * * * *